(12) United States Patent
Beebe et al.

(10) Patent No.: US 6,193,647 B1
(45) Date of Patent: Feb. 27, 2001

(54) MICROFLUIDIC EMBRYO AND/OR OOCYTE HANDLING DEVICE AND METHOD

(75) Inventors: David J. Beebe, Savoy, IL (US); Ian K. Glasgow, Madison, WI (US); Matthew B. Wheeler, Tolono, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 0 days.

(21) Appl. No.: 09/289,137

(22) Filed: Apr. 8, 1999

(51) Int. Cl.[7] .............................. A61B 17/43; A61D 7/00
(52) U.S. Cl. .................................................. 600/33
(58) Field of Search .................... 600/33, 35; 435/7.2

(56) References Cited

U.S. PATENT DOCUMENTS

| | | | |
|---|---|---|---|
| 4,676,274 | 6/1987 | Brown | 137/806 |
| 4,832,759 | 5/1989 | Curtis et al. | 435/285 |
| 5,296,375 | 3/1994 | Kricka et al. | 435/291 |
| 5,304,487 | 4/1994 | Wilding et al. | 435/291 |
| 5,376,252 | 12/1994 | Ekstrom et al. | 204/299 |
| 5,427,946 | 6/1995 | Kricka et al. | 435/291 |
| 5,486,335 | 1/1996 | Wilding et al. | 422/55 |
| 5,498,392 | 3/1996 | Wilding et al. | 422/68.1 |
| 5,512,476 * | 4/1996 | Gordon | 600/33 |
| 5,635,358 | 6/1997 | Wilding et al. | 435/7.2 |
| 5,637,469 | 6/1997 | Wilding et al. | 435/7.21 |
| 5,691,194 * | 11/1997 | Gordon | 600/33 |
| 5,744,366 * | 4/1998 | Kricka et al. | 600/33 |
| 5,757,482 | 5/1998 | Fuchs et al. | 356/246 |
| 5,779,868 | 7/1998 | Parce et al. | 204/604 |
| 5,989,835 * | 11/1999 | Dunlay et al. | 435/7.2 |

FOREIGN PATENT DOCUMENTS

| | | |
|---|---|---|
| 9115750 | 10/1991 | (WO). |
| 9322053 | 11/1993 | (WO). |
| 9322055 | 11/1993 | (WO). |
| 9747390 | 12/1997 | (WO). |

OTHER PUBLICATIONS

M. Lane and D.K. Gardner, "Selection of Viable Mouse Blastocysts Prior to Transfer using a Metabolic Criterion", *Human Reproduction*, vol. 21, No. 9, 1996, pp. 1975–1978.

P.C.H. Li and D.J. Harrison, "Transport, Manipulation, and Reaction of Biological Cells On–Chip Using Electrokinetic Effects", *Analytical Chemistry*, vol. 69, No. 8, pp. 1564–1568, 1997.

N.G. Chan, J.T. Lyman, S.J. Choi, H.C. Zeringue, I.K. Glasgow, D.J. Beebe, M.B. Wheeler, "Development of an Embryo Transport and Analysis System: Material Biocompatibility", *Theriogenology*, vol. 51, No. 1, p. 234, (abstr.), 1999.

S.J. Choi, I. Glasgow, H. Zeringue, D.J. Beebe, M.B. Wheeler, "Development of Microelectromechanical Systems to Analyze Individual Mammalian Embryos: Embryo Biocompatibility", *Biol. Reprod.*, Vol 58 (Suppl. 1), p. 96 (abstr.), 1998.

(List continued on next page.)

*Primary Examiner*—Max Hindenburg
*Assistant Examiner*—Brian Szmal
(74) *Attorney, Agent, or Firm*—Greer Burns & Crain Ltd.

(57) ABSTRACT

A microfluidic embryo handling device and method in which biological rotating of embryos is simulated. Fluid flow is used to move and position embryos without assistance of electrical stimulus or other means which may produce undesired heating of biological medium used as the fluid for transporting and position. Continuous or pulsed flow is maintained around an embryo or embryos in the device. The device provides an excellent simulation of biological conditions and may be used for culturing, sorting, testing, evaluating, fertilizing and other similar typical handling operations. An embryo may be parked at a desired location to carry out such a typical operation, while the microfluidic handling device maintains fluid flow around the embryo.

22 Claims, 5 Drawing Sheets

OTHER PUBLICATIONS

J.M. Lim, B.C. Reggio, R.A. Godke, W. Hansel; "A Continuous Flow, Perifusion Culture System for 8–to 16–Cell Bovine Embryos Derived from In Vitro Culture", *Theriogenology*, vol. 46, pp. 1441–1450, 1996.

J.A. Pruitt, D.W. Forrest, R.C. Burghardt, J.W. Evans, D.C. Kraemer, "Viability and Ultrastructure of Equine Embryos Following Culture in a Static or Dynamic System", *Journal of Reproduction and Fertility*, vol. 44 (Supp.), pp. 405–410, 1991.

C.L.Keefer, S.L. Stice, A.M. Paprocki, P. Golueke, "In vitro Culture of Bovine IVM–IVF Embryros: Cooperative Interaction Among Embryos and the Role of Growth Factors", *Theriogenology*, vol. 41, pp. 1323–1331, 1994.

I.K. Glasgow, H.C. Zeringue, D.J. Beebe, S.J. Choi, J.T. Lyman, M.B. Wheeler, "Individual Embryo Transport and Retention on a Chip", in Micro Total Analysis Systems '98; Proceedings of the TAS '98 Workshop held in Banff, Canada, D.J. Harrison and A. van den Berg, Eds. Boston: Kluwer Academic Publishers, pp. 199–202, 1998.

K. Chun, G. Hashiguchi, H. Toshiyoshi, H. Fujita, "An Array of Hollow Microcapillaries for the Controlled Injection of Genetic Materials into Animal/Plant Cells", presented at Technical Digest of Twelfth IEEE International Conference on Micro Electro Mechanical Systems (MEMS '99), Orlando, FL, 1999, pp. 406–411.

I.K. Glasgow, H.C. Zeringue, D.J. Beebe, S.J. Choi, J.T. Lyman, M.B. Wheeler, "Individual Embryo Transport and Retention on a Chip for a Total Analysis System", presented at the Solid–State Sensor and Actuator Workshop, Hilton Head Island, SC, 1998.

M.B. Wheeler, S.J. Choi, I.K. Glasgow, H.C. Zeringue, J.T. Lyman, D.J. Beebe, "Development of Microelectromechanical Systems to Analyze Individual Mammalian Embryos: Embryo Biocompatibility and Individual Embryo Transport on Silicon A Chip", *Arquivos da faculdade de Veterinaria UFRGS*, Sociedade Brasileira de Transferencia de Embraoes, vol. 26, No. 1, 1998 (Supl), p. 391.

K. Hosokawa, T. Fujii, I. Endo, "Hydrophobic Microcapillary Vent for Pneumatic Manipulation of Liquid in $\mu$TAS", in Micro Total Analysis Systems '98; Proceedings of the TAS '98 Workshop held in Banff, Canada, D.J. Harrison and A. van den Berg, Eds. Boston: Kluwer Academic Publishers, pp. 307–310, 1998.

"Microchip Arrays put DNA on the Spot", *Science*, vol. 282, Oct. 16, 1998, pp. 396–405.

* cited by examiner

▨ SHALLOW REGION
▦ DEEP REGION

MICROFLUIDIC EMBRYO AND/OR OOCYTE HANDLING DEVICE AND METHOD

FIELD OF THE INVENTION

The present invention generally concerns handling of embryos. The invention also concerns handling of oocytes (prefertilized embryos). Embryo, as used herein, therefore encompasses oocytes as well as fertilized embryos. The invention more specifically concerns microfluidic handling of embryos for culturing, manipulation, and analysis.

BACKGROUND OF THE INVENTION

Technology assisted reproduction techniques in which embryos are handled independently from their mammalian biological source are growing in importance and frequency of use. Such techniques have great direct benefit to persons unable to have babies through unassisted sexual reproduction. The agricultural industries also increasingly rely upon such assisted reproduction techniques. Embryo manipulation is used in livestock reproduction to control such things as the faster genetic evolution of cattle and permitting the genetic characteristics of a single exceptional cow or bull to be passed on to far greater numbers of offspring than would be possible through unassisted sexual reproduction.

Livestock embryo manipulation is becoming more routine due to the development of gene manipulation, cloning, and in vitro fertilization (IVF) techniques. The overall goal of embryo manipulation in livestock is to increase production efficiency, especially with regard to reproduction, milk production or production of specific milk components, lean tissue growth with reduced fat content and decreased susceptibility to specific diseases. Embryo transfer is also used to introduce or rescue valuable germplasm and propagate rare breeding animals such as endangered exotic species.

Expense and relatively low success rates place significant burdens on the use of these assisted reproduction techniques for humans as well as livestock. In human reproduction such expense and failure adds emotional as well as economic burdens. In addition, safeguards against failures often result in unwanted or unmanageable multiple births, as well as additional stored embryos which require maintenance and additional difficult decision making at some later point in time. Expense is the primary concern in livestock reproduction.

Failure rates in reproduction techniques as well as testing and other embryo handling techniques are attributable primarily to the significant handling and manipulation of embryos in executing these techniques. Animal reproductive technologies have advanced in recent years, but the physical tools used in animal reproduction have not changed significantly. Fine-bore glass pipets are still one of the basic tools of the embryologist. Using standard petri dishes, procedures such as in vitro maturation of eggs (IVM), in vitro fertilization, and embryo culture (EC) require picking up and placing individual eggs and embryos several times for each procedure.

Such handling and movement from one petri dish to another provides significant potential for damage or contamination. Perhaps more important, though, is the failure of a stationary embryo in a petri dish to simulate the corresponding natural biological reproduction condition. Some efforts have been made to move embryos in petri dishes via agitation of the dish, but this is a haphazard approach. Expense is also created here due to the relatively large amount of biological medium required for the manual petri dish conventional embryo handling methods. Bovine embryos are individually handled with pipets and large, expensive manipulators. Large quantities of biological medium including growth agents for human embryo culturing renders the corresponding in vitro procedure even more expensive. Livestock growth factors, for example, have costs exceeding $200 per 50 µg.

Such static culture systems also fail to allow for changing the milieu in the culture medium as the embryo develops. Current culture systems with flowing medium have culture chambers as small as 0.2 to 0.5 ml. However, the culture volumes are greater than needed and medium is replenished too quickly. The endogenous growth factors that enhance development are diluted out and washed away. The large volumes of medium required substantially increase costs when expensive growth factors, such as IGF-II ($200 per 50 µg) are used. In addition, known systems cannot track individual embryos.

Thus, there is a need for an improved embryo handling device and method which addresses problems in known embryo handling techniques. An improved embryo handling device and method should provide for an improved simulation of natural conditions. It should also provide a building block upon which larger and/or more powerful and accurate instruments may be based, such as embryo culturing systems, embryo analysis systems, embryo storage systems, and similar systems.

SUMMARY OF THE INVENTION

These needs are met or exceeded by the present microfluidic embryo handling device and method. The invention simulates biological rotating of embryos. An embryo fluidic channel moves an embryo inserted therein with fluid, and is sized on the same scale as the particular type of embryo or embryos to be handled. The sizing and fluid communication produces a simulated biological rotating of embryos. In addition, the fluid flow with and around the embryo or embryos prevents stagnation, reducing the likelihood of the embryo or embryos developing "bed sores".

The invention also permits the biological medium fluid to be altered gradually, having significant advantages compared to repeatedly manually transferring an embryo from one medium to another medium in a pipet or petri dish. Gradual changes avoid the shock from sudden changes in local environment. The microfluidic system of the invention further permits the co-culturing of an embryo with other embryos, co-culturing of an embryo or embryos with cells upstream of the embryo(s), and maintenance of a separate control culture that shares a common biological medium with a subject embryo(s) thereby ensuring that test embryos see the same environmental conditions as the subject embryo(s).

BRIEF DESCRIPTION OF THE DRAWINGS

Other objects, features and advantages of the invention will be apparent to artisans who read the detailed description and reference the accompanying drawings, of which.

DETAILED DESCRIPTION OF THE INVENTION

The present invention provides a microfluidic embryo handling device which reduces stress to embryos handled outside their natural biological host. The device and method reproduce simulated biological rotating of an embryo through fluid assisted movement in a channel that encourages embryo slipping and rotating. Rotating, as used herein, may include complete rotation or partial rotation. Partial rotation might also be referred to as a rocking motion.

Figure 1:
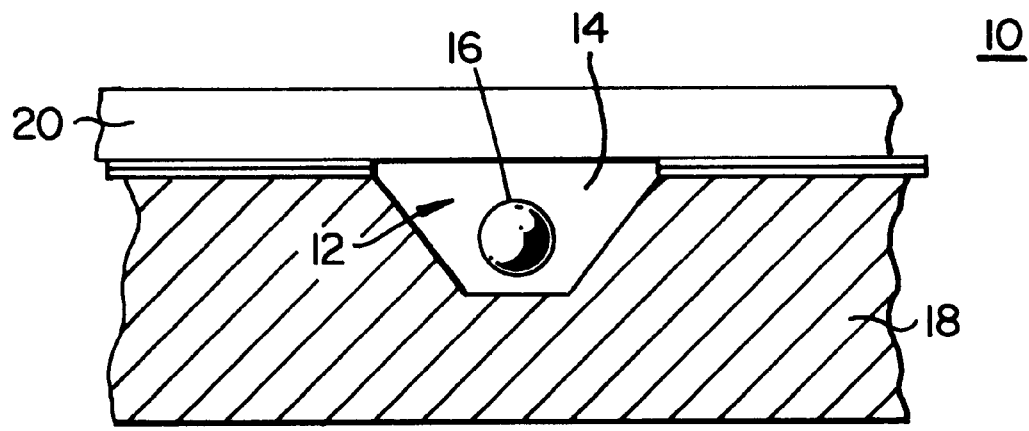
FIG. 1 shows a cross section of a preferred microfluidic embryo handling device constructed in accordance with the present invention.

Referring now to FIG. 1 shown is a cross-section of a microfluidic embryo handling device 10 including a embryo transport network 12 formed at least in part by a generally embryo scale channel 14. An embryo 16 in the channel 14 will move with fluid flow in the channel 14, while the close dimensions of the channel cause the embryo 14 to move with a simulated biological rotating motion. In biological hosts, developing embryos in their initial stages of development move toward the uterus to which they will attach with a rotating and slipping motion. The microfluidic channel 14 produces a simulation of such motion.

Sizing of a channel is important to establish the biological rotating. Height is the critical dimension, and it has been found that heights up to about three times the diameter of an embryo induce the rotating. This ratio may be determined to vary somewhat because fluid flow also plays a role, but the three to one maximum ratio has been found to produce the rotating. It will be appreciated that the channel width is less important. The width may be selected arbitrarily. Thus, if embryos are to be kept in single order, then the width would be less than twice the embryo diameter. If more embryos are desired, larger width channels may be used.

Networks of the channels 14 provide a means to culture embryos, as well as to move and place embryos to desired locations. During its initial stages of development, the size of most mammalian embryos remain generally constant during the first few days after fertilization. Thus, the size of the channels 14 provide no impediment to culturing an embryo therein. Advantageously, the embryo 16 may be kept moving and/or may have a continuous or pulsed fluid flow passed around it to avoid potential detrimental biological effects on the embryo 16.

A preferred exemplary construction of a device 10 including a channel is also illustrated in FIG. 1. The microfluidic channel 14 may be formed by any suitable micromachining technique into a suitable material, such as a silicon wafer 18. The material chosen must be capable of being sterilized and should not pose a biological threat to embryos. The channel (s) 14 of the device are sealed through a cover 20. Forming the cover of glass or other transparent material allows convenient visual monitoring of embryos in channel(s) 14. A bonding agent 22 bonds the cover 20 to the wafer 18. Additionally, the material of the cover could be formulated to shield harmful radiation from the embryo(s) in channel(s) 14.

Unlike other cells that tend to float in a fluid medium, the relatively large and heavy embryos sink to the bottom of the microfluidic channels 14. Typical mammalian preimplantation embryos of interest are 90 to 180 μm diameter spheres. In each embryo, a membrane surrounds each cell (blastomere) and the zona pellucida, a glycoprotein membrane or shell, surrounds the entire cell mass. The cells divide several times during the first few days after fertilization, the volume of the embryo remains constant and an egg may be fertilized and cultured to a blastocyst in the same device constructed based upon the principles of the invention. The blastocyst is the final stage before an embryo implants in the uterus.

Also important to production of such a device and similar devices is the ability to handle individual embryos, or small numbers of embryos. Positioning embryos to given locations, moving to alternate locations, and maintaining constant or changing biological conditions around the embryo(s) are abilities provided by basic principles of the present invention, and permit the construction of fertilization, culturing, testing, and other devices which rely on some or all of those abilities. For continuous movement of an embryo through a culture period of time, long channels may be created, or a loop may be formed. Alternately, a parking of an embryo may occur at a culturing station like those shown in FIGS. 6(a) and 6(b). A compartment or channel of limited size may also be used to roll an embryo back and forth therein by changing fluid flow, as will be further discussed with respect to FIGS. 6(a) and 6(b).

Figure 2A:
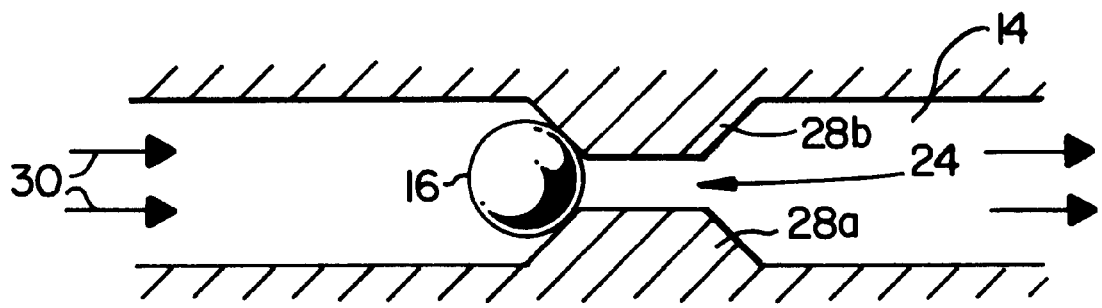
FIG. 2(a) is a top view showing a preferred narrow microfluidic channel constriction for embryo positioning.
Figure 2B:
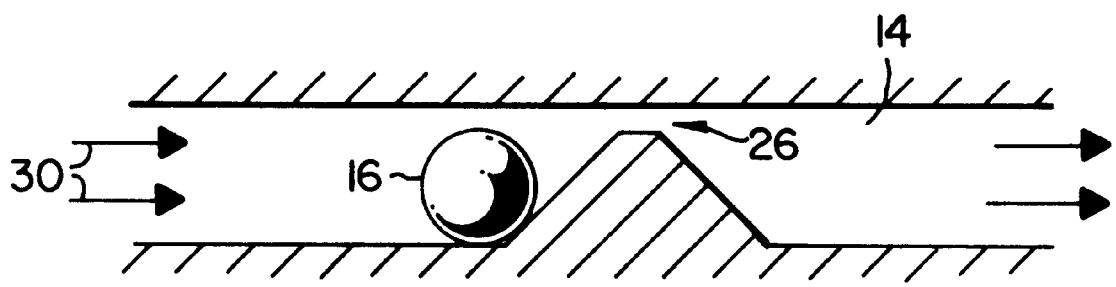
FIG. 2(b) is a cross-sectional view of an alternate preferred shallow microfluidic channel constriction for embryo positioning.

Accurate positioning of individual embryos is provided by the invention through the use of constrictions, preferred examples of which are shown in FIGS. 2a and 2b. FIG. 2(a) is a top view of a cross section of a narrow constriction 24 formed in a microfluidic channel 14. There are many reasons such an accurate positioning may be desirable in an embryo handling device 10. Analysis instruments built into the device may require an embryo to be precisely positioned at electrodes, a photodetector, the focal point of a microscope, or other similar sensing device. Transporting an embryo to the constriction 24 permits such required positioning without resort to feedback systems. An embryo 16 is freed from the constriction 24 simply by reversing the flow of biological fluid medium 30. Even when held at the constriction, an embryo 16 experiences a flow of biological fluid medium around it since fluid 30 will flow past it and through the constriction 24. This is advantageous since an embryo in stagnant fluid has an increased potential to develop "bed sores", a suspected but yet unproven explanation for low success rates in embryo handling technology.

Sidewall portions 28a, 28b of the microfluidic channel 14 constrict it at a desired location to prevent passage of an embryo 16 therethrough. The constriction 24 does not completely close the microfluidic channel 14 so that fluid biological medium 30 may pass an embryo 16 positioned at the constriction 24. FIG. 2(b) shows a side cross-section of an alternate shallow constriction 26 where the fluid biological medium 30 is similarly able to pass when an embryo 16 is positioned at the constriction. Other shapes of constriction are also possible. Generally, any shape which prevents passage of an embryo 16 while simultaneously allowing fluid flow through the constriction, e.g., asymmetric shapes and comb-like fibers, is acceptable to position embryos in a device 10 according to the invention. It is preferred that the constriction be sized such that positioning of an embryo prevents the embryo from passing without an increased pressure from the fluid pressure used in a device 10 to move embryos. Constriction length should also be kept small enough to avoid fluid control problems since the constriction portion of a microfluidic channel will have much higher fluidic resistance per unit length than unrestricted portions of the microfluidic channels 14.

Figure 3:
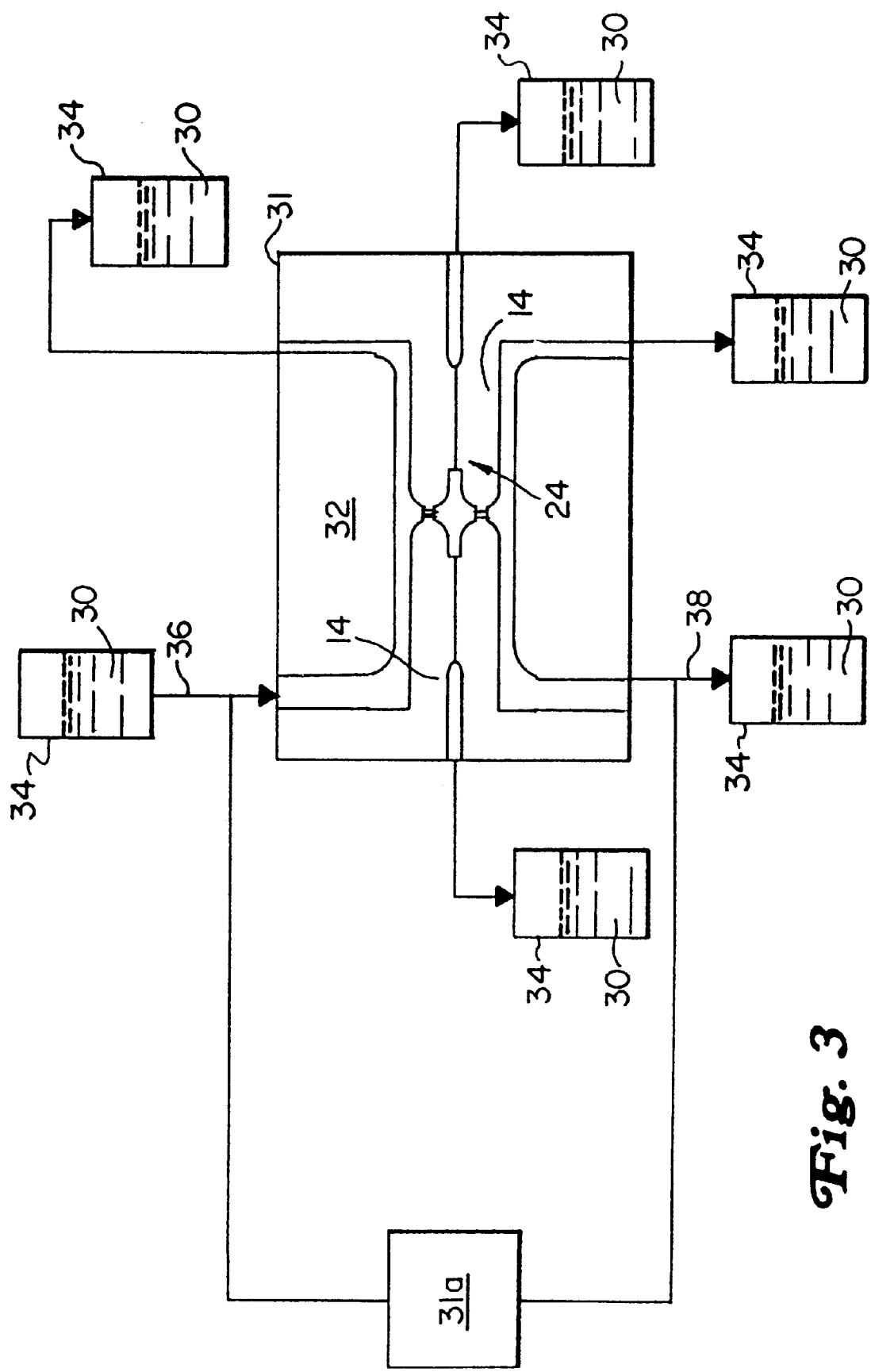
FIG. 3 is a perspective view of a preferred gravity flow driven microfluidic culturing and testing device constructed in accordance with the present invention.

A culture and test device 31 including a constriction like that shown in FIG. 2(a) for positioning an embryo is illustrated in FIG. 3. The device 31 has fluid flow in a network 32 of microfluidic channels 14 driven by gravity based upon levels of fluid 30 in a plurality of fluid reservoirs 34. Any suitable means for driving fluid 30 is contemplated as being compatible with the general principles of the invention, e.g. pumping, but the gravity method illustrated in FIG. 3 is preferred for its simplicity and efficiency. Directions of flows are controlled simply by levels of fluid in reservoirs 34. Thus, for example, an embryo 16 held at a constriction 24 for culturing or examination by a suitable instrument is positioned by first setting fluid levels to cause its travel from inlet port 36 to constriction 24, and is released when fluid flow is reversed through the construction 24. Removal of the embryo 16 is accomplished by causing fluid flow to move it to exit port 38.

During movement through the microfluidic channels 14 of the network 32, the embryo(s) roll and slip to simulate natural movement of embryos toward a uterus in a mammalian host, as discussed above. This desirable manner of moving may be aided by a suitable surfactant such as BSA (bovine serum albumin). The surfactant will help to promote some slippage of the embryo as it rolls.

FIG. 3 also illustrates an additional advantage of the invention, in the provision of a parallel additional microfluidic handling and culturing device 31a. The additional device 31a has a structure similar to that of device 31, but may have fewer or even a single microfluidic channel. Ideally, the structure is the same. The important feature of the device 31a is that it shares a common fluid source with inlet port 36 and outlet port 38 of primary device. Embryo(s) handled in the device 31a are isolated biologically from embryo(s) in primary device 31, but experience the same biological conditions through sharing the same fluidic source, pressure and/or the same biological medium condition. In an exemplary use, the additional device 31a therefore might form an important control culture in which development or lack of development of test embryo(s) could confirm suitability or unsuitability of conditions created in the primary device 31.

Figure 4:
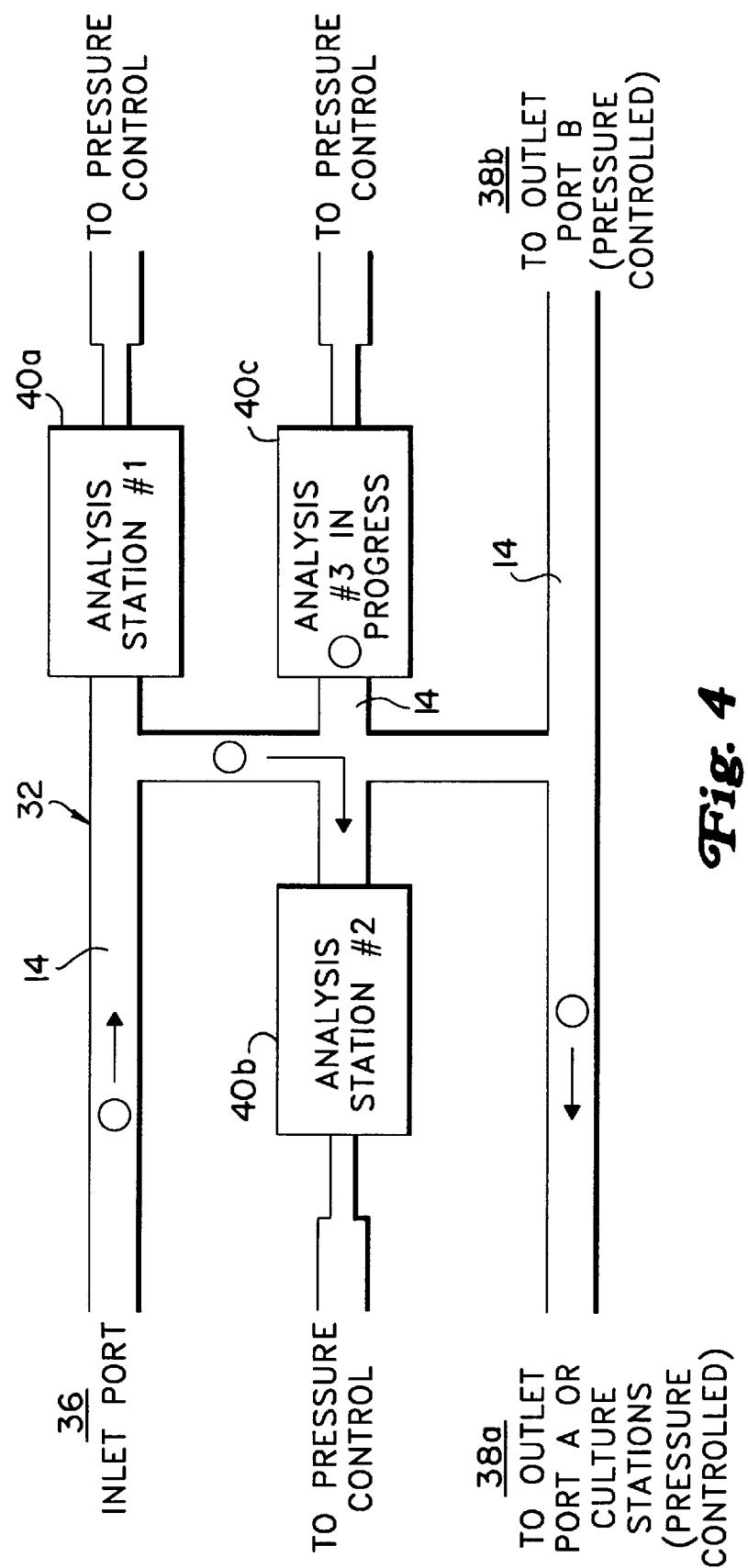
FIG. 4 is a block diagram of an embryo analysis device constructed in accordance with the present invention.

FIG. 4 is a block diagram of an embryo analysis device. In the FIG. 4 device a network 32 of microfluidic channels 14 moves embryos to one or more analysis stations 40a, 40b or 40c. Embryos are positioned at a given analysis station through constrictions like those described above. The analysis stations may include any instrument capable of obtaining information concerning an embryo, with the constriction being formed to position embryos at the proper sensing point for the particular instrument used in an analysis station. Embryos are moved out of the device through one or more exit ports 38a, 38b, which might alternately lead to a culturing station in the form of a parking area for an embryo, an additional length of microfluidic channel 14, or a microfluidic channel loop for continuous movement of an embryo during culturing.

Figure 5A:
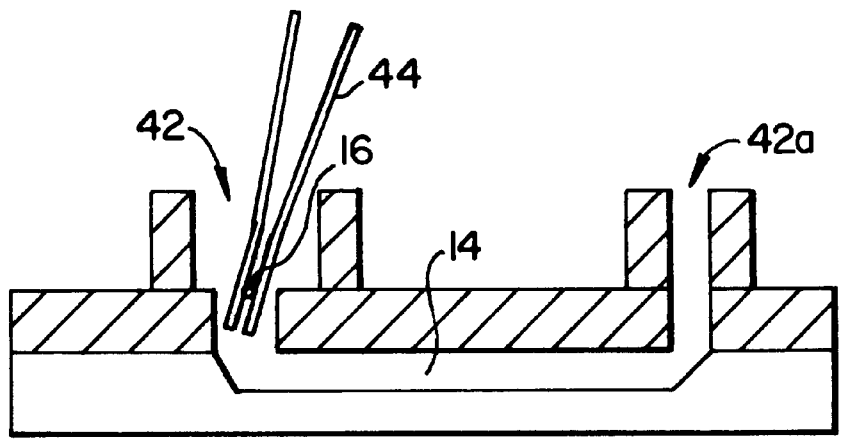
FIGS. 5(a)–5(c) illustrate preferred embryo microfluidic channel insertion and removal structures in accordance with the present invention.
Figure 5B:
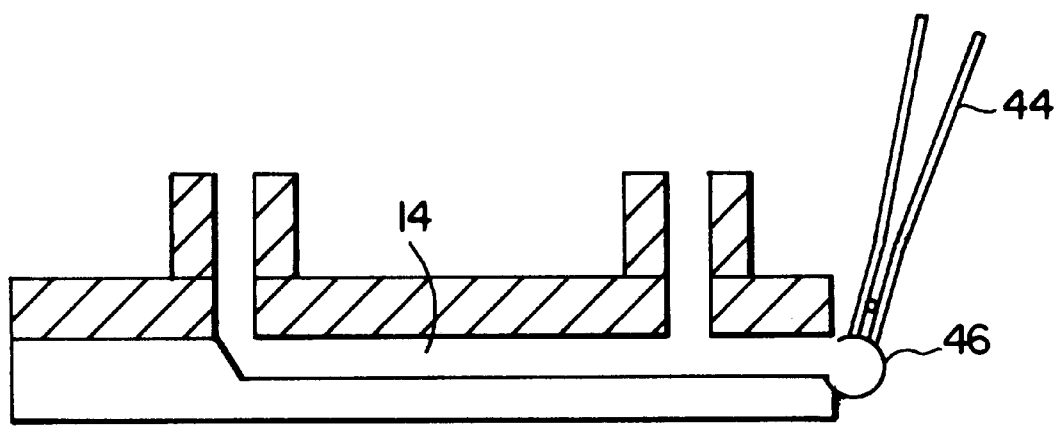
Figure 5C:
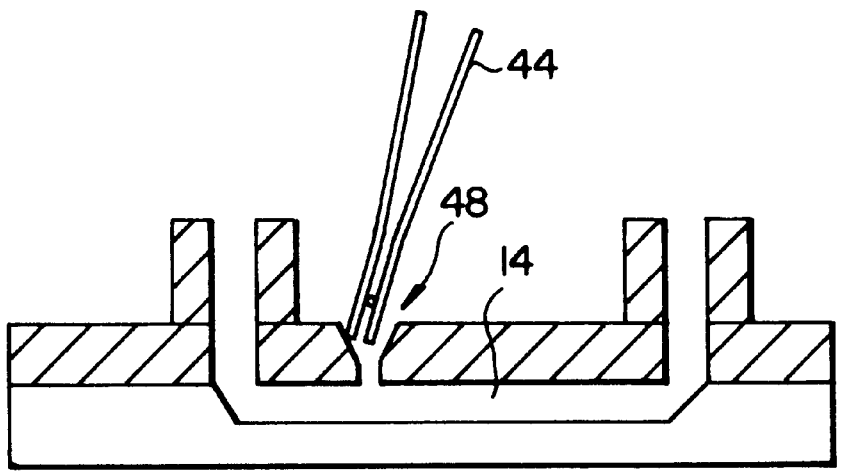

Inlet and outlet ports used in devices of the invention may comprise any conventional manner or structure for embryo insertion or removal. However, additional preferred structures for insertion and removal are shown in FIGS. 5(a)–5(c). In FIG. 5(a), a well 42 which is in fluid communication with a microfluidic channel 14 is used. Fluid in the well 42 preferably also comprises a gravity feed which helps drive microfluidic flow in the channel 14. An embryo 16 is placed in the well 42 and moves into the channel 14 with biological medium, or simply sinks unaided into the channel 14 if no flow condition is created. A second similar well 42 may be used to remove an embryo using a pipet 44 or similar device, which might also be used for insertion. In FIG. 5(b), a hanging drop 46 at the end of a channel 14 is used for insertion and removal. The hanging drop 46 is held by surface tension. After embryo insertion, fluid may be added at that point, or the embryo may be sucked in by fluid flow in the device. Alternately, the device may be inclined to promote embryo movement away from the hanging drop 46. In FIG. 5(c), a funnel shaped hole 48 in direct communication with channel 14 is used for insertion and removal. The funnel shape aids positioning of a pipet 44 or similar device. Surface tension at a small diameter hole 48 will prevent fluid from leaking out, but the pressure in channel 14 must not exceed the point that would defeat surface tension and cause fluid to leak out. Inserted embryos will sink into the channel 14, while removal may be accomplished by drawing fluid from hole 48 when an embryo approaches. Of course, any of the FIG. 5 techniques may be combined with each other or conventional techniques for insertion and removal in a given handling device. In addition, the wells 42 or holes 48 may be covered by a removable cover or flap as protection against contamination and/or evaporation.

Figure 6A:
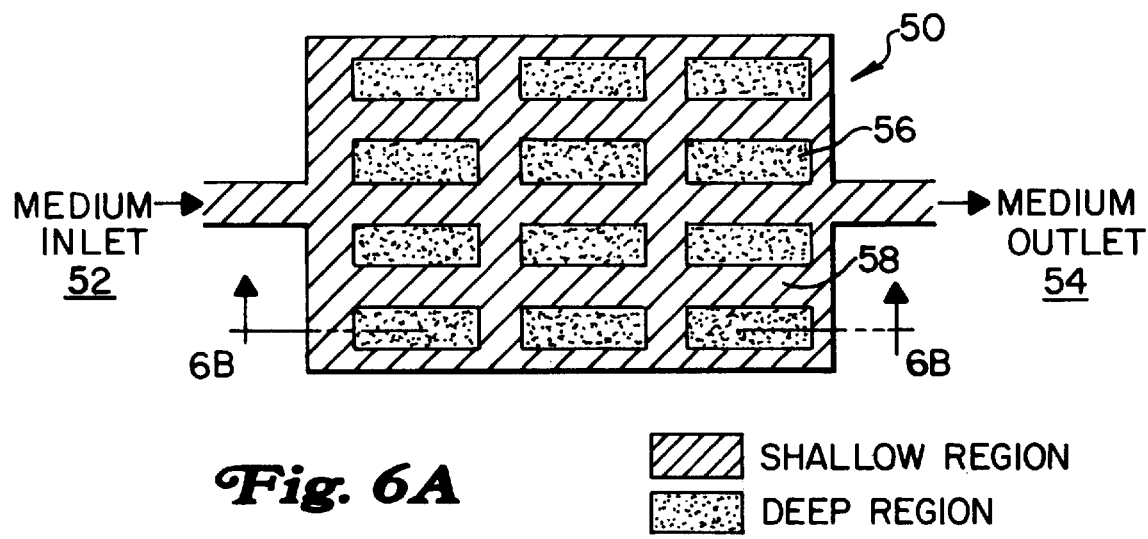
FIGS. 6(a)–6(b) illustrate a preferred culturing device constructed in accordance with the present invention.
Figure 6B:
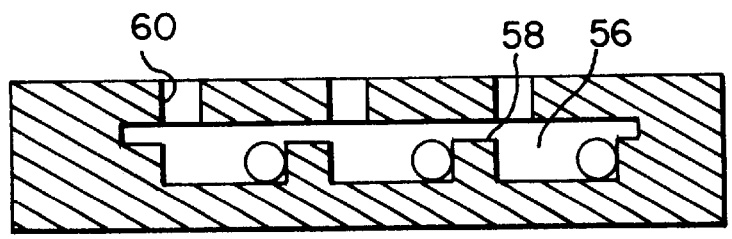

Referring now to FIGS. 6(a) and 6(b), an embryo culturing device 50 according to the present invention is shown. Fluid medium flow in the culture device 50 is in either direction between a medium inlet 52 and a medium outlet 54. The device includes a number of traps or compartments 56. As best seen in FIG. 6(b), the traps 56 comprise deep regions separated by shallow regions 58. Fluid flow between inlet 52 and outlet 54 is over shallow regions and through deep regions to move embryos back and forth within the deep region compartments 56. Embryos are inserted and removed through access holes 60, which may be formed by any of the preferred methods in FIGS. 5(a) through 5(c). In the device 50, artisans will thus appreciate that embryos may be moved back and forth within compartments 56 to simulate biological rotating, may experience the same medium conditions as other embryos within the culture, and may be easily removed and inserted. Though FIGS. 6(a) and 6(b) show a top loading embodiment for placing embryos within the compartment, the device will also work in a bottom loading arrangement, essentially inverted from that shown in FIGS. 6(a) and 6(b). In such a bottom loading arrangement, the embryos will still be held in the deep portions but cannot pass the shallow portions. An alternate embodiment might comprise a gap in place of shallow constructions where embryos cannot pass through the gaps but fluid flow may occur therebetween and the depth of the gaps may be the same as those of the embryo holding compartments.

Prototype devices like that shown in FIG. 3 have been produced and tested. Typical prototypes are described here for the sake of completeness. Artisans will appreciate that the manner of fabricating the prototypes may be accomplished by any other convention microfabrication techniques. Artisans will also appreciate that production device manufacturing may differ significantly, and that specific numerical dimensions and conditions of the prototype devices do not limit the invention in the breadth described above.

In typical prototype channels, a pressure gradient of 1 Pa/mm causes the medium to flow on the order of $10^{-10}$ $m^3/s$ (100 nl/s), with an average speed of 1 to 2 mm/s. Under these flow conditions the embryos roll along the bottoms of the channels; traveling at speeds ranging from ⅓ to ½ that of the fluid that would otherwise be in the same region of the channel. By manipulating the pressure at the wells connected to the ends of the channels, the embryos can be transported to (and retained at) specific locations including culture compartments and retrieval wells. Embryos fill a considerable portion of the channel, thereby greatly altering the flow of medium. The flow of medium through the channels is laminar.

Networks of prototype microfluidic channels have been fabricated in a device like that shown in FIG. 3 by etching trenches in 3-inch <100> silicon wafers, and then bonding glass covers to form channels. Typical channel networks contain several branch microfluidic channels that intersect near the center of the device. The branches, which range from 1.5 to 2.5 cm in length, are 160 to 200 μm deep and 250 to 350 μm wide at the top. A first step in producing prototype devices involves patterning silicon nitride (SiN) coatings on using conventional photolithography techniques. The microfluidic channels are anisotropically etched with a potassium hydroxide (KOH) solution. Access holes in the glass covers are drilled, either conventionally using carbide tipped bits or ultrasonically. Glass covers are bonded to the wafers using UV curable epoxy (NOA 61, Norland Products, Inc, New Brunswick, N.J.) or Pyrex 7740 covers are anodically bonded to the wafers using 500V in a 450° C. environment. The nitride coatings are removed using buffered oxide etchant (BOE) before anodic bonding. Glass wells are bonded to the glass cover at the end of each branch of the channel network with either an epoxy (Quick Stick 5 Minute Epoxy or 5 Hour Set Epoxy Glue; both from GC Electronics, Rockford, Ill.) or a silicone adhesive (RTV 108 and RTV 118 from General Electric Co., Waterford, N.Y., or Sylgard® Brand 184, Dow Corning Corp., Midland, Mich.).

In the prototype devices, constrictions like those in both of FIGS. 2(a) ("narrow") and 2(b) ("shallow") have also been fabricated and tested. Channels with "narrow" constrictions, as shown in FIG. 2(a), can be fabricated using a single mask and etching operation. Channels with the "shallow" constrictions, as shown in FIG. 2(b), require two masks and two etching operations.

All the component materials of the prototype devices except the five minute epoxy were tested for embryo biocompatibility. In applying the present invention, artisans will appreciate that alternate materials may be used from those selected for the prototype devices, but biocompatibility must always be established through prior data and/or testing. Although many materials are known to be compatible with or toxic to certain cells, little work has been done to investigate the compatibility of materials used in micro fabrication with embryos. The materials selected may also vary depending upon the type of mammal from which the specific embryos to be handled are taken.

In prototype testing, two-cell mouse embryos (B6SJL/F2) were randomly assigned to and cultured on the substrata, in medium M16 (Sigma, St. Louis, Mo.) with bovine serum albumin (BSA; 4 mg/ml; Sigma), covered with mineral oil (Sigma). All embryos were cultured at 37° C. in a 5% $CO_2$ in air atmosphere for 96 h. Developmental rates of embryos were examined every 24 h. The percentage of embryos that reached the blastocyst stage for each material was compared with the percentage from the control group. Mouse embryos that reach the blastocyst stage, the latest possible stage before embryo transfer, are probably not developmentally hindered. While the absence of negative effects is not guaranteed unless the embryos are also transferred to recipient mice and monitored until the offspring are born, tests are commonly concluded at the blastocyst stage for practical and economic reasons. Most of the materials tested proved to be compatible with the mouse embryos, including silicon wafers, SiN coatings, NOA 61, and RTV 118. Some materials, such as the 5-minute epoxy, have not been tested since it is only used in conceptual devices to demonstrate mechanical and fluidic principals of the invention, and would likely not be used in production devices.

Tests were run to examine several aspects of the prototype devices. Different tests required devices with different channel configurations. In all the tests, a halogen bulb via optical fibers illuminated the channel, which was viewed under a stereomicroscope. A graduated cylinder and a stopwatch were used to determine flow rates. Since the fluid is incompressible, the average fluid velocity in any section of channel is just the flow rate divided by the cross-sectional area.

Measurements of the rate of travel of the embryo for a given flow rate occurred in a simple straight channel, 29 mm long, 162 μm deep, and 160–380 (bottom—top) μm wide. The pressure gradient was varied and the speed of the embryo was measured for each setting. The channels were filled with phosphate buffered saline (PBS), with and without BSA. Flasks of the medium were connected to the channel. By adjusting the heights of the flasks, using micrometer head translation stages, the pressure difference was finely tuned to within 0.05 Pa. The flasks were connected to each other by tubing between the tests to zero the pressure head. The microfabricated prototype devices were cleaned in a hydrogen peroxide/ammonium hydroxide/deionized water solution and new pipet tips were adhered with epoxy before the tests were conducted. All the tests using PBS without BSA were conducted before those with BSA. Once the channels were filled with medium the mouse embryos were placed in the inlet well, at the channel entrance.

Tests were run to observe the influence of channel size and shape on the transport of embryos. For these tests, a device was fabricated with one long, circuitous channel with 11 sections each at one of four depths: 140, 164, 194, and 210 μm. At each depth the channel has 2 or 3 different widths. Widths, measured at the surface of the wafer, range from 275 to 480 μm. In the narrowest segments, the embryos were geometrically constrained to travel on a V-groove while in the other regions along a flat-bottomed channel. The speed of travel and rotating characteristics were observed and compared for different segments.

Observations of embryos at constrictions occurred in several devices, with both narrow and shallow type constrictions. Embryos were actually directed to specific constrictions. Altering the height of the medium in each well, by adding or subtracting fluid, tailored the pressure gradients in each branch of the channel network. Pressure heads were adjusted by a 1 to 8 mm (10 to 80 Pa).

Just as embryos placed in medium sink to the bottom of the container, embryos placed in microfluidic channels settle to the bottom. In all the tests, when the medium flowed, the embryos rolled and slid along the bottom of the channel in the direction of flow. Often they also remained in contact with one of the side walls of the channel. In initial tests without any surfactant in the medium (phosphate buffered saline) the embryos appeared to roll without slipping along the bottoms of the channels. Embryos slid or rolled with slip along the bottoms in later tests when the medium contained BSA (4 mg/ml).

Tests revealed that the rate of travel of an embryo in a channel depends upon the velocity of the medium. Sometimes they stick to the bottom of the channel when the velocity of the fluid around them is below 50 µm/s. For both media, PBS and PBS/BSA, a pressure gradient of 0.16 Pa/mm drives the flow through the channel at an average velocity of approximately 380 µm/s. The embryos rolled at 187–250 µm/s, 49 to 66% of 380 µm/s. As the medium flows more quickly, the embryos roll faster, slipping as they roll. The actual speed of travel and the tendency to stick varies from one embryo to the next One embryo has been observed to travel 25% quicker than another at the same time in the same channel, in almost the same path line. In the observed range, 150 to 1000 µm/s, the velocity is linear with pressure gradient.

Results from testing the effects of channel size and shape match a priori predictions. For a given flow rate, the average fluid velocity and embryo speed is greater in a channel with smaller cross-sectional area. In contrast, for a given pressure gradient, the average fluid velocity and embryo speed is greater in a channel with larger cross-sectional area. In both cases, embryos travel slower on V-grooves than on flat-bottomed channels. Embryos are also more likely to become wedged and stuck in a V-groove than on a flat-bottomed channel.

Fluid under electroosmotic flow also caused embryos to roll through channels. An embryo rolled along the channel bottom at approximately 10 µm/s due to the pressure driven trickle flow. Switching on the voltage caused the mouse embryo to roll along the channel bottom 20 µm/s faster, at approximately 30 µm/s, toward the well with the negative electrode. With the voltage polarity reversed, the embryo rolled at approximately 10 µm/s in the reverse direction. No surfactant, such as BSA was used so there was little or no slipping. Electric assistance was determined to be undesirable due to its heating of the medium.

Computational fluid dynamics modeling using Fluent/UNS 4.2 (Fluent, Inc., Lebanon, N.H.) and 2-dimensional finite element analysis of prototype microfluidic channels with constant cross-section using Quickfield (Tera Analysis, Inc., Tarzana, Calif.) verified the observed flow rates and flow patterns. The embryo was modeled as a rigid sphere. Recall that the embryo does not appear to deform under typical conditions. To analyze the laminar flow, 1 or 2 mm sections of channel were meshed into 10,000 to 30,000 tetragonal elements. Once verified, computer modeling was used to determine flow velocity profiles, design constrictions with lower pressure drops, to observe forces on embryos retained at constrictions, and to analyze electrically driven flows in similar channels. However, analysis incorporating adhesion of the embryo to the channel walls and distortion of the embryo would be significantly more complex and was not attempted.

As discussed above, in the straight channel tests of embryo velocity, the medium had an average velocity of 380 µm/s under a pressure gradient of 0.16 Pa/mm. Finite element analyses determined the centerline velocity to be 815 µm/s under these conditions. When traveling in the channel, the embryo was tangent to the bottom and one wall. Consider a 100 µm diameter circle tangent to the bottom and one side of the channel. The average velocity of the fluid traveling through this circle when the embryo is not present is 480 µm/s. However, the embryos rolled at only 187–250 µm/s, 39–52% as quickly, in both PBS and PBS/BSA media. The velocity profile encourages the embryo to roll forward and along the wall, which confirms visual observations. In sum, embryos roll at ⅓ to ½ the speed at which fluid would flow in the same region of the cross section.

The constrictions greatly increase fluidic resistance in the channels. Standard analytical formulas can help approximate the resistance, but the cross-sectional shapes of the constrictions vary with position. Three-dimensional models of the constrictions were analyzed before masks were designed and wafers were etched. The information gained from the finite element analyses led to optimally-sized constrictions. The shallow constrictions, sized individually for the geometry of the device, balance the need for minimal flow resistance and robust fabrication. Typical constrictions have a minimal depth of 20 µm.

Studies of the placement of the embryos at the traps reveal lateral forces on the order of $10^{-8}$ to $10^{-7}$ N force the embryo to the side and part way up the ramp at the entrance to the shallow constriction.

The tests revealed several interesting characteristics of microfluidic transport, such as variations in velocity between embryos and the tendency to roll along the bottoms of the channels, often tangent to a side wall. However, the testing did reveal several other issues, Electrical control of fluid flow was investigated initially, but the high voltages harm the embryos in several ways. Even with the embryos in sections of channel away from the electric fields, the applied energy heats up the medium (Joule heating) beyond physiological temperatures and the electrolysis products alter the pH. Note that an embryo requires about 0.029 Osmol, i.e., a relatively high conductivity. Also, EOF is degraded in channels with surfactant, but the embryos survive better in medium with a surfactant, such as BSA.

Microfluidic transport free of electrical assistance offered through gravity fed devices like that in FIG. 3, or through pumped fluid pressure devices, offers an important advantage. The medium can be easily altered with time to meet the changing requirements of the developing embryos. Gradually changing the composition of the medium avoids inducing stresses upon the embryo from the abrupt environmental changes that often accompany transfer from one petri dish to a second dish with a different medium. The microfluidic handling of embryos by the invention is not physically harsher than transfer with pipets and definitely less damaging than many techniques in conventional practice including some which pierce the outer membrane.

It is anticipated that control of fluid flow, and therefore embryo positioning, in handling devices like that shown in FIG. 3 will be handled through programmed control instruments for largely automated devices. Alarms and warnings may be incorporated based upon sensed conditions within an embryo handling device of the invention. In similar fashion, monitoring of embryos with conventional instruments applied to a handling device of the present invention. Artisans will generally recognize that the microfluidic embryo handling device thus forms a basic building block upon which many useful devices may be based, and that such devices will incorporate the essence of the present invention.

While various embodiments of the present invention have been shown and described, it should be understood that other modifications, substitutions and alternatives are apparent to one of ordinary skill in the art. Such modifications, substitutions and alternatives can be made without departing from the spirit and scope of the invention, which should be determined from the appended claims.

Various features of the invention are set forth in the appended claims.

What is claimed is:

1. A microfluidic embryo handling device comprising:
an embryo transport network having a biological medium for movement of embryos inserted therein, said transport network including an approximate embryo scaled embryo fluidic channel to facilitate simulated biological rotating of individual embryos moving within said fluidic channel.

2. The microfluidic embryo handling device of claim 1, wherein said transport network is formed in a wafer and said embryo fluidic channel comprises a microchannel in said wafer.

3. The microfluidic embryo handling device of claim 1, further comprising:
a biological medium source for introducing said biological medium into said embryo transport network in a continuous flow manner; and
a control test embryo network fed said biological medium from said biological medium source, said control test embryo network being biologically isolated from said embryo transport network.

4. The microfluidic embryo handling device of claim 1, further comprising:
a gravity controlled biological medium source for introducing said biological medium into said embryo transport network in a continuous flow manner.

5. The microfluidic embryo handling device of claim 1, further comprising a formation in a path defined by said communication channel for holding an embryo at a desired location while maintaining flow of said biological medium past an embryo held at said desired location.

6. The microfluidic embryo handling device of claim 5, wherein said formation comprises a constriction.

7. The microfluidic embryo handling device of claim 6, further comprising:
a biological medium source for maintaining flow of said biological medium and for reversing flow of said biological medium to free an embryo held at said desired location.

8. The microfluidic embryo handling device of claim 1, wherein said fluidic channel has a flat bottom.

9. The microfluidic embryo handling device of claim 1, wherein said fluidic channel has a V-shaped bottom.

10. The microfluidic embryo handling device of claim 1, wherein said simulated biological rotating includes rotating and slipping.

11. The microfluidic embryo handling device of claim 1, further comprising:
a controlled biological medium source for introducing said biological medium into said embryo transport network in a continuous flow manner unassisted by electrical stimulus.

12. The microfluidic embryo handling device of claim 1, wherein movement of embryos in said embryo transport network is unassisted by electrical stimulus.

13. The microfluidic embryo handling device of claim 1, wherein said transport network is sealed from surrounding environment and said device further comprises an embryo entrance to said transport network and an embryo exit from said transport network.

14. The microfluidic embryo handling device of claim 13, wherein said embryo entrance comprises a hole penetrating a sealing member which seals said transport network, said hole maintaining separation between said biological medium and surrounding environment through surface tension.

15. The microfluidic embryo handling device of claim 14, further comprising a removable cover to seal said hole.

16. The microfluidic embryo handling device of claim 14, wherein said hole is funnel shaped.

17. The microfluidic embryo handling device of claim 14, wherein said hole is located in a midstream portion of said transport network.

18. The microfluidic embryo handling device of claim 13, wherein said embryo entrance comprises a well in fluid communication with said transport network.

19. The microfluidic embryo handling device of claim 13, wherein said embryo entrance comprises a hanging drop.

20. The microfluidic embryo handling device of claim 1, wherein said fluidic channel comprises an embryo compartment defining a culturing station for an embryo and said device further comprises smaller than embryo diameter fluid flow channels for moving fluid through said embryo compartment.

21. A microfluidic embryo handling device, comprising:
a fluid path for moving an embryo inserted therein by fluid flow unassisted by electrical stimulus;
surfaces defining at least a part of said fluid path and spaced to promote rotating of said embryo as it moves in said fluid path.

22. A method of handling embryos comprising steps of:
moving an embryo through exclusive use of fluid flow;
rotating said embryo as said step of moving is executed.

* * * * *

UNITED STATES PATENT AND TRADEMARK OFFICE
CERTIFICATE OF CORRECTION

PATENT NO. : 6,193,647 B1  
DATED : February 27, 2001  
INVENTOR(S) : Beebe et al.

Page 1 of 1

It is certified that error appears in the above-identified patent and that said Letters Patent is hereby corrected as shown below:

<u>Column 10,</u>  
Line 21, delete "issues, Electrical" and insert -- issues. Electrical -- therefore <u>Column 11,</u>  
Line 29, delete "communication" and insert -- fluidic -- therefore Signed and Sealed this Fifth Day of February, 2002

Attest:

JAMES E. ROGAN  
*Director of the United States Patent and Trademark Office*

*Attesting Officer*